United States Patent [19]

McDavid et al.

[11] Patent Number: 5,018,177

[45] Date of Patent: May 21, 1991

[54] APPARATUS AND METHOD FOR PRODUCING DIGITAL PANORAMIC X-RAY IMAGES

[75] Inventors: W. Doss McDavid; S. Brent Dove, both of San Antonio, Tex.; Ulf Welander, Umea; Gunilla Tronje, Enskede, both of Sweden

[73] Assignee: Board of Regents, The University of Texas System, Austin, Tex.

[21] Appl. No.: 360,093

[22] Filed: Jun. 1, 1989

[51] Int. Cl.$^5$ .............................................. G01N 23/04
[52] U.S. Cl. ...................................... 378/62; 378/146; 378/39
[58] Field of Search ...................... 378/21, 22, 38–40, 378/146, 62

[56] References Cited

U.S. PATENT DOCUMENTS

| | | | |
|---|---|---|---|
| 3,495,084 | 2/1970 | Sheldon | 250/370.09 |
| 3,932,756 | 1/1976 | Cowell et al. | 378/39 |
| 4,021,672 | 5/1977 | Franke | 378/39 |
| 4,039,837 | 8/1977 | Ohta et al. | 378/39 |
| 4,100,417 | 7/1978 | Goetzl et al. | 378/38 |
| 4,179,100 | 12/1979 | Sashin et al. | 378/19 |
| 4,188,537 | 2/1980 | Franke | 378/39 |
| 4,239,971 | 12/1980 | Cushman | 378/39 |
| 4,259,721 | 3/1981 | Kuznia . | |
| 4,628,356 | 12/1986 | Spillman et al. | 358/111 |
| 4,661,967 | 4/1987 | Nishikawa | 378/39 |
| 4,692,937 | 9/1987 | Sashin et al. | 378/62 |
| 4,709,382 | 11/1987 | Sones | 378/146 |
| 4,823,369 | 4/1989 | Guenther et al. | 378/39 |
| 4,845,731 | 7/1989 | Vidmar et al. | 378/146 |
| 4,878,234 | 10/1989 | Pfeiffer et al. | 378/40 |

FOREIGN PATENT DOCUMENTS

| | | |
|---|---|---|
| 215757 | 3/1987 | European Pat. Off. . |
| 279293 | 8/1988 | European Pat. Off. . |
| 279294 | 8/1988 | European Pat. Off. . |
| 0279294 | 2/1988 | Fed. Rep. of Germany . |
| 236478 | 5/1978 | France . |
| 2459649 | 1/1981 | France . |

OTHER PUBLICATIONS

Journal of the International Association of Dento-Maxillo-Facial Radiology, 1985, Publication on Imaging Characteristics of Seven Panoramic X-Ray Units (McDavid, et al).
Chapter 16 of Textbook of Dental Radiology (Landland, et al.) addresses "Rotational Panoramic Radiography".

Primary Examiner—Carolyn E. Fields
Assistant Examiner—David P. Porta
Attorney, Agent, or Firm—Arnold, White & Durkee

[57] ABSTRACT

Apparatus and method for producing a digital panoramic X-ray image of an object is disclosed. The system of the invention includes an X-ray source and a digital radiation detector, which move around the object in unison in a certain time period. The radiation detector produces pixel data signals that are proportional to the incident X-rays on it. The pixel data signals are integrated over a series of varying time intervals to obtain pixel data signals which are proportional to the X-rays incident upon the radiation detector during each time interval. The integrated pixel data signals are converted into digital signals, which are then used to produce a digital X-ray image of the object.

12 Claims, 4 Drawing Sheets

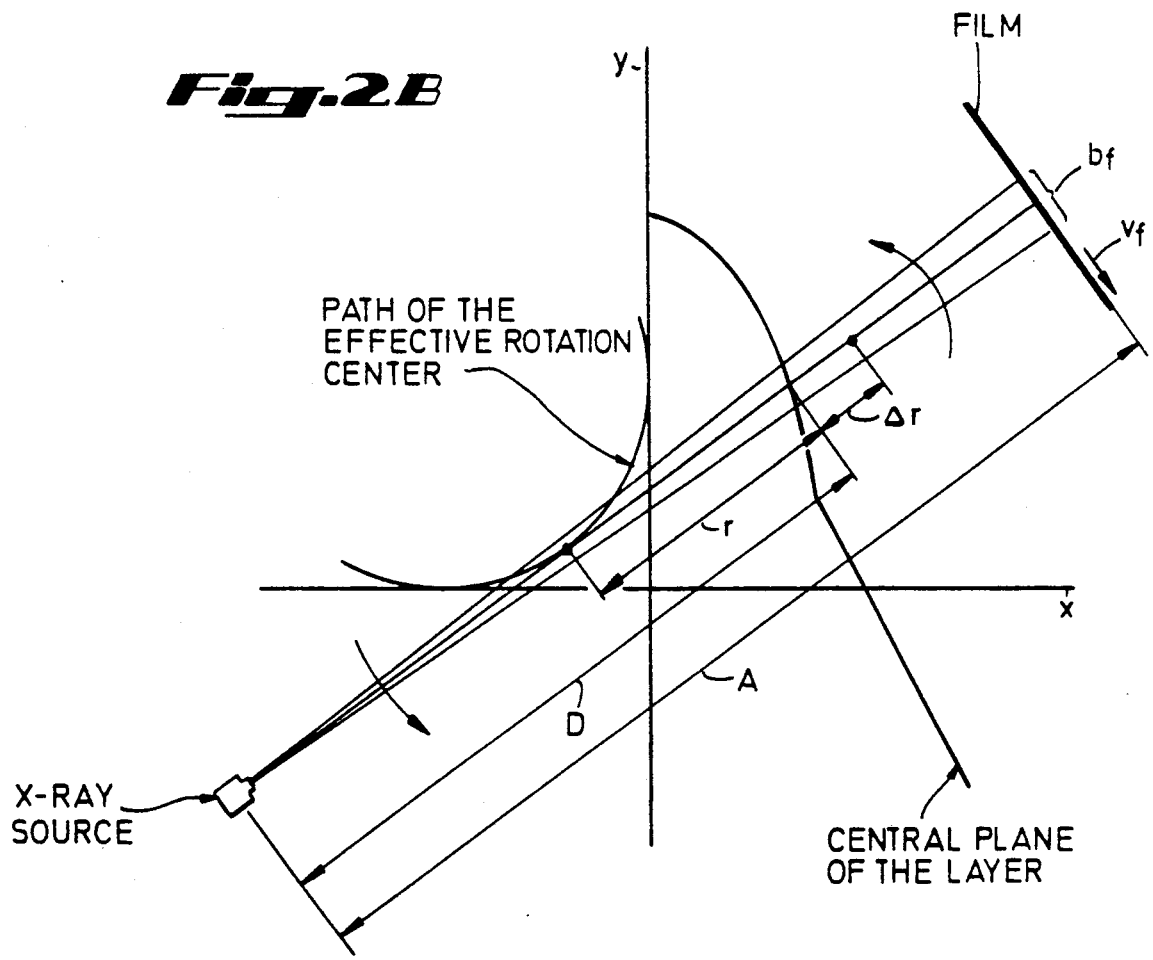

APPARATUS AND METHOD FOR PRODUCING DIGITAL PANORAMIC X-RAY IMAGES

BACKGROUND OF THE INVENTION

The present invention relates generally to digital X-ray imaging and more particularly to panoramic digital X-ray imaging in the field of dental diagnostics.

Conventional apparatus and methods for obtaining a panoramic X-ray image or radiograph or X-ray shadow of the maxillo-facial region utilize rotational panoramic radiography using an external X-ray source. This is accomplished by allowing a narrow vertical X-ray beam to move in a transverse plane around a rotational axis which is positioned inside the mouth of the patient. The X-ray image of the maxillo-facial region is projected on a radiographic film. The radiographic film is moved in the transverse plane and also relative to the X-ray beam. Because of the uneven curvature of the maxillo-facial complex, the film speed is varied to match the vertical and horizontal magnifications of the X-ray projection. This technique provides a relatively undistorted X-ray image of the maxillo-facial area on a radiographic film.

Several manufacturers currently market radiography machines (X-ray machines) that produce high quality (relatively undistorted) panoramic radiographs of the maxillo-facial region. All of these machines use a rotating X-ray beam and a moving film. The center of rotation for each type of machine can vary. Some machines utilize a fixed center of rotation, some utilize a continuously moving center of rotation, and yet some others utilize a combination of the two. However, each type of machine utilizes a predetermined scanning geometry, film speed, focal spot size and X-ray beam width. The combination of these parameters produces a unique image layer for each rotational-type panoramic radiography equipment. The image layer has a central plane for which the X-ray image is sharpest and least distorted. The manufacturers of such equipment have attempted to design an image layer which conforms in its overall geometry to the structure of the dental arch, which is sufficiently wide so as to provide a reasonably sharp portrayal of that anatomy.

Although these systems provide sufficiently undistorted radiographs, they still require the use of photographic films and photographic processing and developing equipment to produce the image of an object. As a result, the users of these radiography equipment must still deal with cumbersome and expensive film processing equipment. With the availability of high resolution electronic radiation detectors, and with the advancement of digital signal processing and imaging techniques, it has become possible to create and store X-ray images digitally. Such systems do not use X-ray films. Various sensors and techniques have been developed to produce digital X-ray images. The present invention provides an apparatus and a method for obtaining digital panoramic X-ray radiographs by utilizing a linear sensor array with variable data acquisition periods in order to provide an image with proper proportion both in the horizontal and vertical dimensions.

SUMMARY OF THE INVENTION

The system of the invention contains an X-ray source, which is moved around an object about a rotational axis in a predetermined time period. A radiation detector, placed at a fixed distance from the X-ray source, detects X-rays that pass through the object and produces pixel data signals proportional to the incident radiation. The predetermined time period is divided into a series of time intervals. The pixel data signals are first integrated during each time interval and then converted into corresponding digital data signals at the end of each time interval. The digital signals are then used to produce a digital image of the object.

Examples of the more important features of this invention have thus been summarized rather broadly in order that the detailed description thereof that follows may be better understood, and in order that the contribution to the art may be better appreciated. There are, of course, additional features of the invention that will be described hereinafter and which will also form the subject of the claims appended hereto.

These and other features and advantages of the present invention will become apparent with reference to the following detailed description of the preferred embodiment thereof in connection with the accompanying drawings wherein like reference numerals have been applied to like elements.

BRIEF DESCRIPTION OF THE DRAWINGS

FIG. 2B shows the geometrical relationship of the critical parameters (A, D, r, $\Delta r$ $V_f$) for a panoramic radiography system having a moving center of rotation that utilizes a radiographic film.

DESCRIPTION OF THE PREFERRED EMBODIMENT

Figure 1:
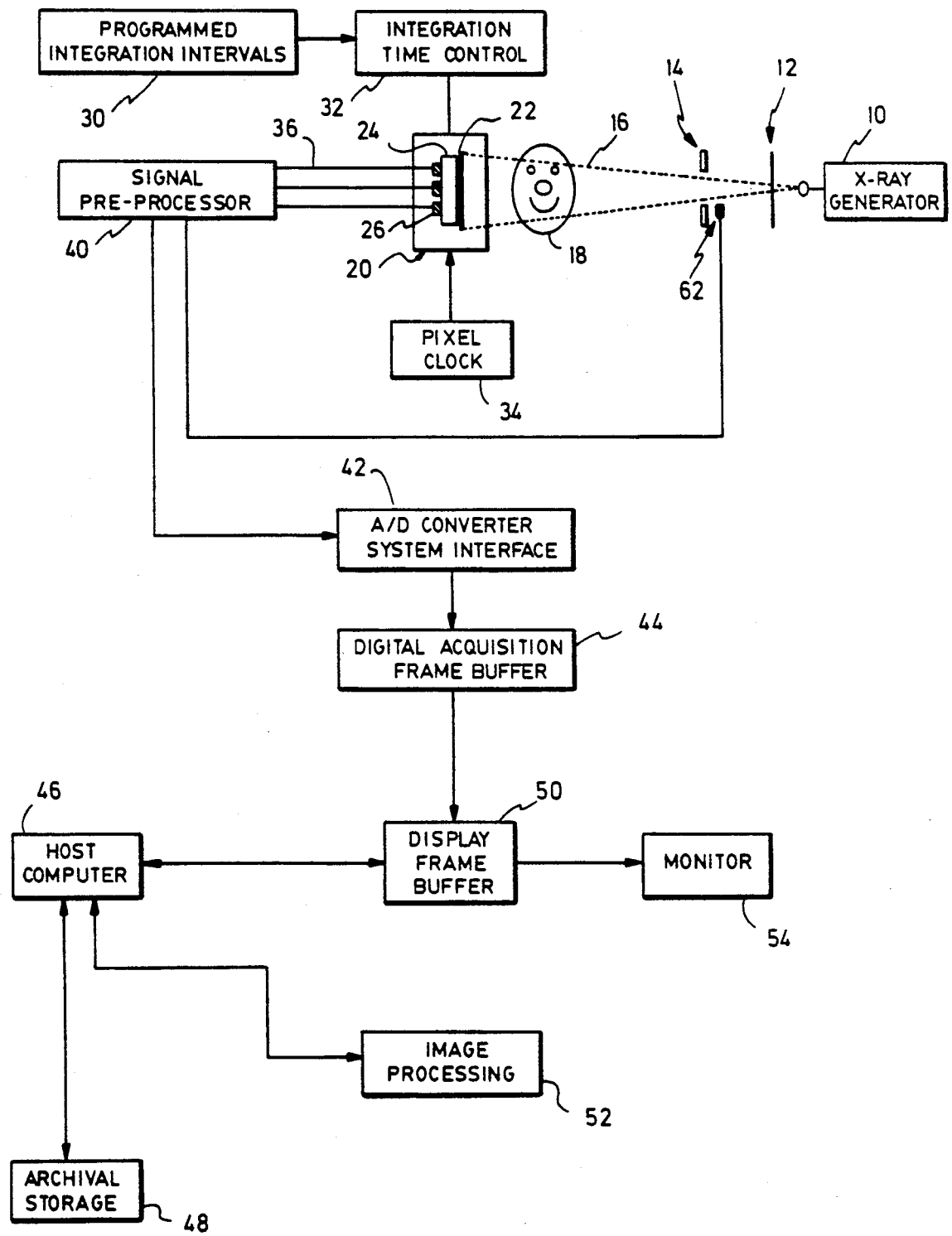
FIG. 1 is a schematic block diagram of the system of the present invention.

FIG. 1 shows the schematic block diagram of the functions performed by the system of the present invention. In the preferred embodiment, this invention contains an X-ray generator or a source that is moved around an object along a predetermined path in a predetermined time period, a digital radiation detector for producing a column of pixel signals proportional to the incident radiation on it, means to integrate the pixel signals over a predetermined number of varying time intervals, means for converting the pixel signals to corresponding digital data, and means for electronically capturing, processing and displaying the digital data, to produce a relatively undistorted X-ray image of a properly positioned object.

As illustrated in FIG. 1, the system of the invention utilizes an X-ray generator 10 to produce the desired level of X-ray radiation. The X-rays are filtered through a filter 12 and then collimated by a collimator 14 to produce a narrow vertical X-ray beam 16. The collimated X-ray beam 16 is projected on to an object 18. The X-rays that pass through the object 18 are projected onto a radiation detector 20, which is aligned with the X-ray source so that the X-ray beam falls directly on it. During radiography of the object 18, the position of the radiation detector 20 remains fixed relative to the X-ray source 10.

The radiation detector 20 contains a scintillator screen 22. The scintillator screen 22 produces light which is proportional to the amount of radiation impinging on it. A linear sensor array 26, such as a linear photodiode array, is either coupled directly to the scintillator screen 22 or by a light coupling means 24, such as optical fibers. The purpose of this is to transfer light from the scintillator screen 22 to the linear sensor array 26 both efficiently and without any significant attenuation. The linear sensor array 26 produces a column (or a set) of pixel data signals, wherein each pixel data signal is proportional to X-rays impinging on a certain area of the scintillator screen 22. The pixel data signals are analog electrical signals. A photodiode type linear sensor array continues to integrate or accumulate each pixel data signal as a function of the amount of light received by its corresponding photodiode until that photodiode reaches a saturation point or until the data is dumped or transferred out of the linear sensor array.

High resolution and efficient linear sensor arrays are currently available commercially. For the purpose of this invention, any suitable high-resolution efficient linear sensor array will suffice. The inventors have built a prototype digital radiography system that practices the present invention. That prototype utilizes a 1024 element linear photodiode array. The prototype produces 1024 pixel data signals, one each corresponding to each photodiode. During operation the 1024 pixel data signals are dumped out of the photodiode array at the end of predetermined time intervals.

For panoramic radiography of an object, such as the maxillo-facial region of a patient, the X-ray source 10 and radiation detector 20 are moved in unison around the object. The X-ray source 10 and the radiation detector 20 move along a transverse plane in a predetermined time period (elapsed time). This elapsed time is divided into a series of time intervals, which are stored in a memory device 30, such as an EPROM. An integration time control means 32, which is an integration clock, is electrically coupled with the device 30 and the radiation detector 20 to control the integration of pixel signals during each time interval. At the end of each time interval, the sensor array produces a vertical column (set or an array) of discrete analog electrical signals (pixel signals), wherein each signal represents the integrated (accumulated) incident X-ray radiation on an area of the radiation detector 20. Thus, if, for example, the linear sensor array has "M" photodiodes, there will be M pixel signals at the end of each time interval, each signal being proportional to the integration of the X-ray radiation impinging upon an area of the X-ray detector 20. If the total time period of the movement of the X-ray source is divided into "N" time intervals, there will be N columns of M pixel data signals, wherein each column will correspond with X-ray radiations passing through the object during one of the "N" time intervals. The duration of each time interval may vary. The method of computing the duration of each time interval is discussed in greater detail later in this specification.

At the end of each time interval, the integrated pixel data signals from the linear sensor array 26 are outputted to a signal preprocessor 40 by a pixel clock 34. The pixel clock 34 and the radiation detector 20 are triggered by the integration time control circuit 32 to dump the pixel data signals into the preprocessor 40. It will be noted that after the pixel data signals have been transferred to the preprocessor at the end of each time interval, the radiation detector 20 starts over to integrate the pixel data signals until they are dumped out at the end of the next successive time interval. In this way, the column or set of pixel data signals at the end of each time interval represents the signals accumulated only for that time interval.

The signal preprocessor 40 amplifies the pixel data signals. The amplified pixel data signals—which are analog signals—are fed to a high speed analog-to-digital converter ("A/D Converter") system interface 42, which converts them into digital data or signals.

The digital data from the A/D converter system interface 42 is fed to a host computer 46 through a digital acquisition frame buffer 44 and a display frame buffer 50. The host-computer 46 interacts with the display frame buffer 50, and an archival storage 48 to produce a digital image on a monitor 54. The X-ray image of the object is stored into the archival storage 48 for future reference.

The digital acquisition frame buffer 44 acquires binary number signals from the sensor 20 for each pixel data point and transfers that data to the display frame buffer 50. The display frame buffer 50 stores the data for display in both the horizontal and vertical direction of the monitor 54. The display frame buffer also produces analog signals corresponding to the digital data for displaying the image on the monitor 54.

The archival storage device 48 can be any one of a number of commercially available or custom made data storage devices that is capable of storing large amounts of data, such as magnetic and optical disk storage devices and the like. In the system of the present invention, combination of the host computer 46, the display frame buffer 50, and the digital acquisition buffer provides the means to electronically process the digital data signals to produce the X-ray image of an object. It will be noted that the components of the system described herein may be easily changed or substituted to accomplish the desired result, that is, to format, store, process, etc., the digital data signals to produce the digital X-ray image of an object.

To enhance the quality of the image that is projected onto the monitor 54, image processing techniques (software) may be used. Block 52 shows that such a technique may be employed in the system of this invention. The science of image processing is a mature science. A number of techniques for enhancing an image are currently in use. Any one of these techniques may be used for the purposes of this invention. Also, for the purposes of this invention, any one of a number of available computers and display frame buffers can be utilized to produce a satisfactory X-ray image of a desired object.

The method of computing the duration of time for each time interval will now be explained in greater detail. The basic concept is to simulate the variable film speed employed in conventional photographic film type panoramic radiography equipment for use in a stationary X-ray detector type radiography equipment.

In conventional panoramic radiography equipment used for producing X-ray images of the maxillo-facial region, the film is moved at a varying speed while the X-ray beam moves around the patient's head. Because of the uneven curvature of such an object, the film speed must be varied so as to closely match the horizontal magnification with the vertical magnification of the X-ray projection to obtain a relatively undistorted image. But, in the system of the present invention, the radiation detector 20 is stationary with respect to the X-ray source 10, although both these devices move during the taking of an X-ray image of the maxillo-facial region of the patient. Therefore, in order to obtain an undistorted X-ray image of an object that has an irregular curvature with apparatus of the present invention—in which the X-ray source remains stationary with respect to the radiation detector—it is necessary to simulate the film movement. In the present invention, the film movement is simulated by varying the integration time for successive columns of pixel signals.

Figure 2A:
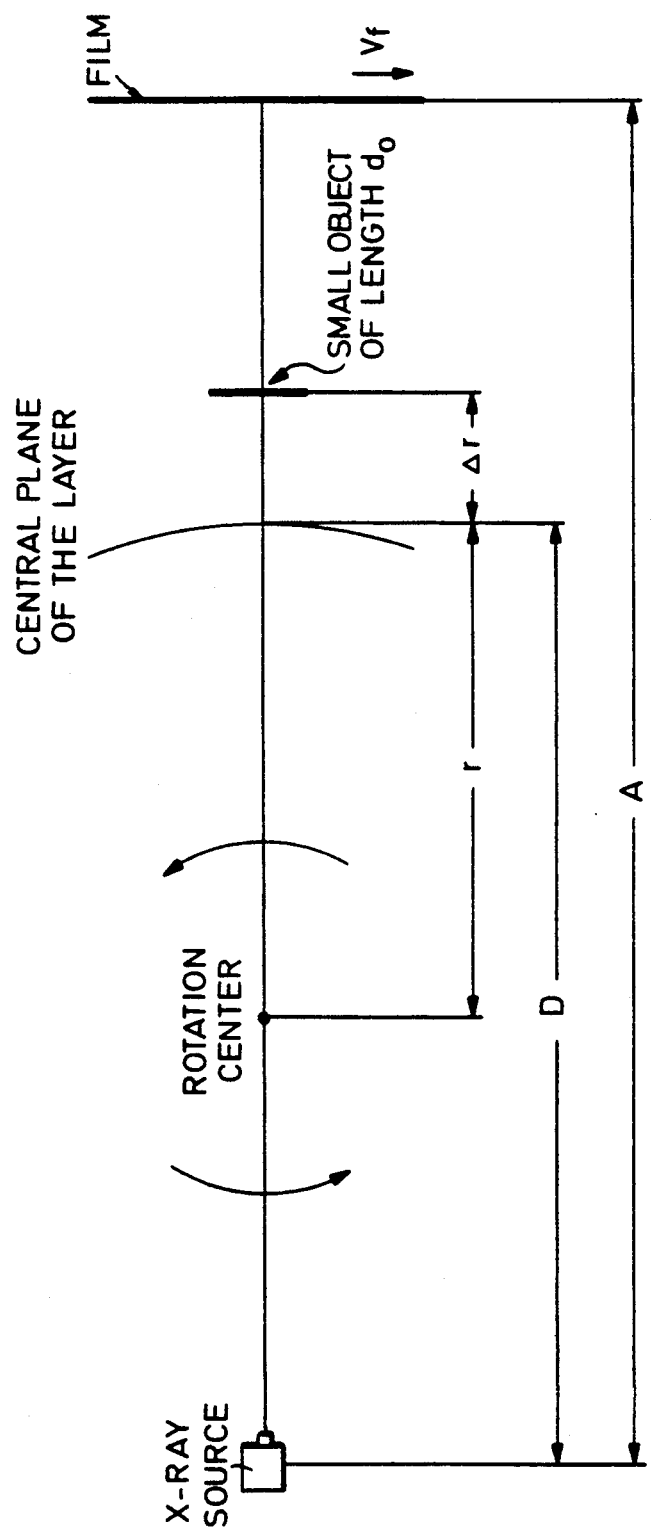
FIG. 2A shows the geometrical relationship of the critical parameters (A, D, r, $\Delta r$, $V_f$) for a panoramic radiography system having a fixed center of rotation that utilizes a radiographic film.

FIG. 2A shows the relationship of critical parameters that are used to determine the number of time intervals and the duration of each time interval, which are used to control the operation of the linear X-ray sensor array in order to properly simulate the film speed.

Still referring to FIG. 2A, a conventional panoramic radiographic equipment utilizing a photographic film, the X-ray source is placed at a fixed distance A from the photographic film. The X-ray source is rotated around a rotation center R, which is at a distance r from the central plane of the image layer of the object. The distances from the central plane of the image layer to the X-ray source and the object are represented by D and $\Delta r$ respectively. During operation, the film moves at a speed $V_f$ with respect to the X-ray beam. The speed of the film is given by $$v_f = \frac{A r \omega_o}{D} \quad (1)$$

where $w_o$ is the angular velocity of the X-ray beam. Under these circumstances, the horizontal magnification, $M_d$, and the vertical magnification, $M_h$, are given by the following equations:

$$M_d = \frac{Ar}{D(r + \Delta r)} \quad (2)$$

$$M_h = \frac{A}{D + \Delta r} \quad (3)$$

The horizontal and vertical magnification factors will be equal for objects in the central plane of the image layer, that is when $\Delta r = 0$; each type of magnification will have a value of A/D. Images of objects in this plane will therefore be undistorted. When $\Delta r$ is not equal to zero, equations (2) and (3) predict the distortion in panoramic radiography, i.e. a widening of objects placed between the central plane and the rotation center R and a narrowing of objects placed between the central plane and the film.

Using a linear array of detectors instead of a moving film, an undistorted image of objects in the central plane can be obtained by choosing the integration time for each successive column of pixels or picture elements equal to $$\tau = \frac{P}{v_f} \quad (4)$$

where P is the effective width of the pixels and $v_f$ has the value $Ar\omega_o/D$ as given above.

Consider the situation shown in FIG. 2A where a rotating X-ray beam of negligible width scans across a small object of length $d_o$. The time required for the beam to traverse the object is $$t = \frac{d_o}{(r + \Delta r)\omega_o} \quad (5)$$

During this time, the number of pixel columns integrated will be $t/\tau$ and the depicted width of the object, $d_f$, will be $Pt/\tau$. Substituting from equations (1), (4), and (5) gives the following as the depicted width of the object:

$$d_f = \frac{Ard_o}{D(r + \Delta r)} \quad (6)$$

$d_f/d_o$ gives the horizontal magnification factor for the panoramic radiography (Equation (2)). The vertical magnification factor is not affected by the rotation or the digital data acquisition and is given by Equation (3) just as before.

The preceding analysis is given for simplicity in terms of the movement of the X-ray beam about a stationary center of rotation with fixed parameters as shown in FIG. 2A. The same principle, however, applies when the effective center of rotation is moving and the various parameters are changing as shown in FIG. 2B. In this case the integration time, $\tau$, varies throughout the data acquisition to form the image of a curved plane at the distance r from the moving effective center of rotation.

Figure 3A:
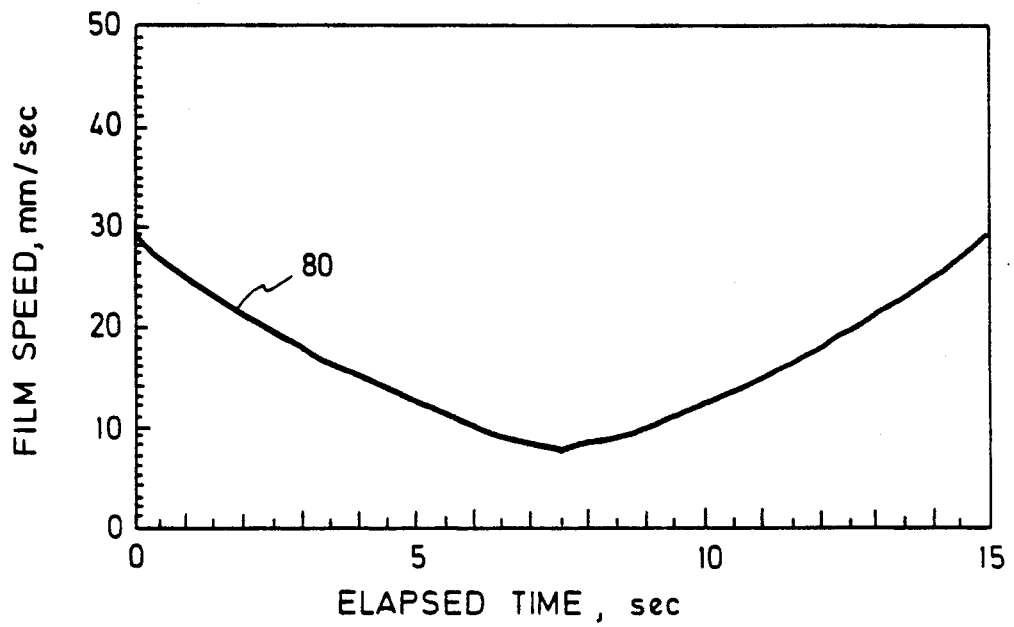
FIG. 3A shows, for a conventional radiography system, a relationship between speed of the radiographic film relative to the beam and the elapsed time during panoramic X-ray imaging of a maxillo-facial region.

FIG. 3A illustrates the relationship between the elapsed time (in seconds) of a moving X-ray source around the maxillo-facial region of a patient and the corresponding film speed (in mm./sec.) for film type radiography equipment, wherein the effective center of rotation is moving. Here, the X-ray is moved from one end of the face (near one ear of the patient) to the other end of the face (near the other ear of the patient). The film speed is shown by trace 80. The film speed is minimum when the X-rays are projected on the front portion of the patient's face and it is maximum when the X-rays are projected on either end of the face.

Figure 3B:
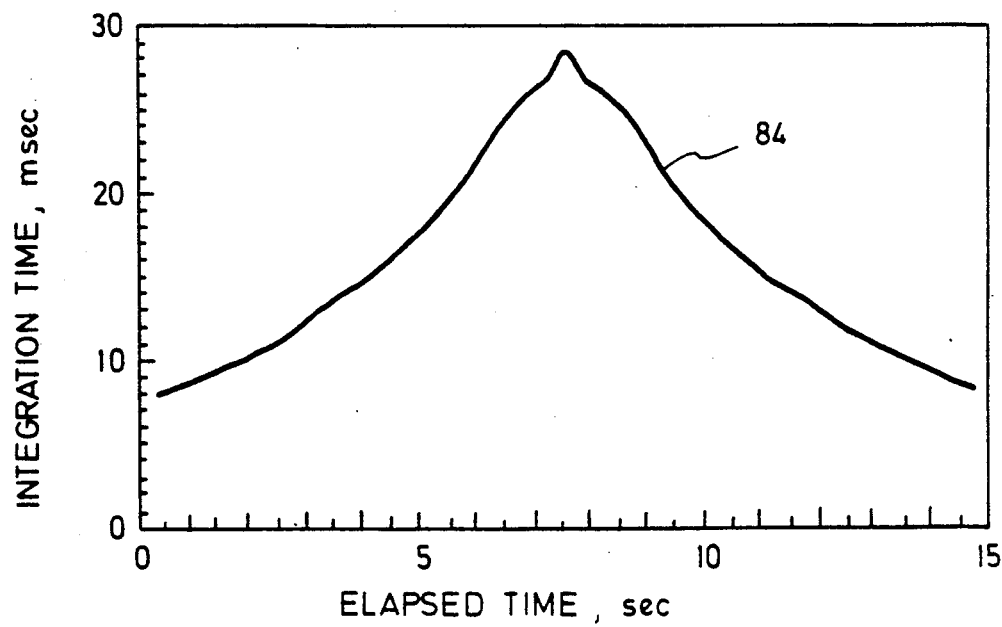
FIG. 3B shows, for a digital radiography system, a relationship between the integration time and the elapsed time during the panoramic imagering of a maxillo-facial region.

FIG. 3B illustrates one example of the integration time for a stationary linear sensor array that corresponds with the film speed of FIG. 3A. Trace 84 of FIG. 3B indicates that the integration time is the largest when the film speed is minimum and that the integration time is smallest when the film speed is maximum. In other words, the integration time, $\tau$, for a fixed sensor varies inversely with the film speed for conventional radiographic film type radiography equipment.

In short, in the present invention, the elapsed time, is divided into "N" intervals and the film speed is simulated by varying the integration time.

The foregoing description has been directed to particular embodiments of the invention in accordance with the requirements of the patent statutes for the purposes of illustration and explanation. It will be apparent, however, to those skilled in the art that many modifications and changes in the apparatus and method set forth will be possible without departing from the scope and the spirit of the invention. It is intended that the following claims be interpreted to embrace all such modifications and changes.

What is claimed is:

1. A method of producing an X-ray image of an object, said method comprising the steps of:

(a) impinging an X-ray beam on the object, the X-ray beam moving about the object along a predetermined path within a predetermined time period;

(b) detecting the X-rays which pass through the object with a single linear radiation detector extending substantially perpendicular to said predetermined path, said radiation detector producing a set of pixel electrical signals, each pixel electrical signal being proportional to X-rays received by an area of the radiation detector;

(c) dividing the predetermined time period into a series of time intervals, said time intervals being a function of an elapsed time of said predetermined time period;

(d) integrating said pixel electrical signals during each time interval; and (e) electronically processing the integrated pixel electrical signals to produce the X-ray image of the object.

2. The method of claim 1 wherein said radiation detector includes a scintillator screen and a linear photo diode array.

3. The method of claim 2 wherein said linear photo diode array has 1024 photodiodes.

4. A method of producing an X-ray image of the maxillo-facial area of a patient, said method comprising the steps of:

(a) impinging a narrow vertical X-ray beam onto the maxillo-facial area of the patient, said X-ray beam moving about the maxillo-facial area in a predetermined path to scan it in a predetermined time interval;

(b) detecting the X-rays that pass through the maxillo-facial area by a single linear detector array extending substantially vertically, said linear detector array producing a set of discrete analog electrical signals, wherein each analog electrical signal is proportional to the X-rays received by an area of the linear detector array;

(c) dividing the predetermined time interval into a series of time intervals, said time intervals being a function of an elapsed time of said predetermined time interval;

(d) integrating the discrete analog electrical signals during each time interval;

(e) amplifying and converting each integrated electrical signal into a corresponding digital signal; and (f) electronically processing the digital signals to produce the X-ray image of the maxillo-facial area.

5. A method of producing an X-ray image of the maxillo-facial area of a patient, said method comprising the steps of:

(a) impinging a narrow X-ray beam on the maxillo-facial area of the patient, said narrow X-ray beam moving in a transverse plane around the patient's face in a predetermined time period;

(b) detecting the X-rays that pass through the maxillo-facial area of the patient by a single linear sensor array, said linear sensor array remaining stationary with respect to the X-ray beam and extending substantially perpendicular to said transverse plane, said linear sensor array also producing a plurality of analog electrical signals which are proportional to the amount of X-rays passing through the maxillo-facial area;

(c) dividing the time period into a series of time intervals, said time intervals being a function of an elapsed time of said predetermined time period;

(d) integrating or accumulating the analog electrical signals during each time interval and producing integrated analog electrical signals which are proportional to the X-rays detected by the linear sensor array during each said time interval;

(e) converting each integrated analog signal into a corresponding digital signal;

(f) electronically processing said digital signals to produce the digital X-ray image of the maxillo-facial area.

6. A method of producing an X-ray image of an object, said method comprising the steps of:

(a) projecting an X-ray beam at the object;

(b) moving the X-ray beam about the object in a plane during a predetermined time period;

(c) detecting the X-rays that pass through the object with a single linear X-ray detector extending substantially perpendicular to said plane;

(d) converting the detected X-rays into a set of discrete electrical signals;

(e) dividing the time period into a series of time intervals and storing these time intervals in a memory device, each of said time intervals being a function of an elapsed time of said predetermined time period;

(f) separately integrating each discrete electrical signal over one of said time intervals, the integration being controlled by an integration clock which cooperates with the time intervals stored in said memory device, said integration clock operating at a fixed frequency;

(g) transferring the integrated discrete electrical signals to a preprocessor at the end of each time interval by a pixel clock means, said pixel clock means being electrically coupled to and cooperating with the X-ray detector, said preprocessor amplifying said integrated discrete electrical signals;

(h) converting the amplified discrete electrical signals into their corresponding digital signals; and (i) electronically processing the digital signals to produce an X-ray image of the object.

7. A method for producing an X-ray image of an object, said method comprising the steps of:

(a) projecting a moving X-ray beam onto the object to scan it in a certain elapsed time, said X-ray beam also moving in a plane about a moving center of rotation;

(b) detecting X-rays that pass through the object by a single linear radiation detector extending substantially perpendicular to said plane, said detector producing a sequence of pixel signals which are proportional to the incident radiation impinging on said detector;

(c) dividing the elapsed time into a series of N time intervals, said time intervals varying in duration;

(d) integrating the sequence of pixel signals during each time interval and transferring the integrated sequence of pixel signals at the end of each said time interval so as to produce N sequences of pixel signals;

(e) converting each of the N sequences of pixel signals into a corresponding digital data; and (f) processing said digital data by utilizing an image processing technique to produce an X-ray image of the object.

8. A method of producing an X-ray image of an object, said method comprising the steps of:

(a) projecting a moving X-ray beam through the object onto a single linear X-ray detector, said X-ray beam moving about a moving center of rotation to scan the object in a certain elapsed time;

(b) said X-ray detector producing a sequence of M discrete analog signals which are proportional to the intensity of the X-ray projecting onto the X-ray detector;

(c) dividing the certain elapsed time into a series of N time intervals and storing them int a memory device, said time intervals being a function of an expired portion of said certain elapsed time;

(d) integrating the sequence of M discrete analog signals during each of the N time intervals to provide an integrated sequence of M discrete signals at the end of each time interval which is proportional to the X-rays projected on to the X-ray detector during that time interval;

(e) transferring the integrated sequence of M discrete analog signals at the end of each said time interval to a preprocessor by a pixel clock, said preprocessor amplifying the integrated sequence of M discrete analog signals; and (f) converting the amplified discrete signals into digital signals by an analog-to-digital converter; and (g) electrically processing the digital signals by using image process techniques to produce an enhanced X-ray image of the object.

9. Apparatus for producing a digital X-ray image of an object, said apparatus comprising:

(a) an X-ray generator for producing a narrow vertical beam of X-rays;

(b) a single linear X-ray detector extending vertically which produces a single column of pixel signals proportional to the X-rays impinged upon it;

(c) integration control circuit, said integration control circuit coupled to the linear X-ray detector, said integration control circuit enabling the linear detector to integrate the pixel signals over a predetermined number of varying time intervals, whereby one column of integrated pixel signals is provided for each time interval;

(d) a pixel clock, said pixel clock coupled to the X-ray detector, said pixel clock enabling said X-ray detector to transfer out said column of integrated pixel signals from said X-ray detector to a preprocessor coupled to the X-ray detector, said preprocessor amplifying said columns of pixel signals;

(e) a high speed analog to digital converter coupled to said preprocessor for converting each said column of amplified integrated pixel signals into a corresponding set of digital signals;

(f) digital data processing means to process each said set of digital signals to produce an X-ray image of the object.

10. A method of producing a panoramic X-ray image of an object by a panoramic radiography apparatus, said apparatus having a movable X-ray source placed at a fixed distance A from a single linear sensor detector, said radiography apparatus defining an image layer of the object at a distance D from the X-ray source, said image layer having a central plane, said central plane defining a plane where the X-ray image of the object is least distorted, said method comprising the steps of:

(a) impinging an X-ray beam from the X-ray source onto the object place between the X-ray source and the single linear sensor detector;

(b) moving the X-ray source around the object in a predetermined time period at an angular velocity of $\omega_o$ about an effective rotational center, said rotation center being at a distance r from the central plane of the image;

(c) detecting the X-rays that pass through the object by the single linear sensor detector and producing a single column of pixel signals, each pixel signal being proportional to the X-rays received by an area of the detector, each said area being of effective width P;

(d) dividing the predetermined time period into a series of variable time intervals $\tau$, said time intervals computed by the relation $$\tau = \frac{P}{V_f}$$

wherein $V_f$ is a function of A, D, r and $\omega_o$; and (e) integrating each pixel signal during the variable time intervals to produce a set of integrated pixel signals at the end of each variable time interval thereby producing pixel signals proportional to the amount of the X-rays received by their respective areas of the detector during each said variable time interval.

11. A method of producing a panoramic X-ray image of an object by a panoramic radiography apparatus, said apparatus having a movable X-ray source placed at a fixed distance A from a single linear sensor detector, said radiography apparatus defining an image layer of the object at a distance D from the X-ray source, said image layer having a central plane, said central plane defining a plane where the X-ray image of the object is least distorted, said method comprising the steps of:

(a) impinging an X-ray beam from the X-ray source onto the object placed between the X-ray source and the single linear sensor detector;

(b) moving the X-ray source around the object in a predetermined time period at an angular velocity of $\omega_o$ about an effective rotation center, said rotation center being at a distance r from the central plane of the image layer;

(c) detecting the X-rays that pass through the object by the single linear sensor detector and producing a single column of pixel signals, each pixel signal being proportional to the X-rays received by an area of the detector, each said area defining a single pixel element of effective width P;

(d) dividing the predetermined time period into a series of variable time intervals $\rho$, said time intervals computed by the relation $$\tau = \frac{P}{V_f}$$

wherein $V_f$ is a function of A, D, r and $\omega_o$; and (e) integrating each said pixel signal during the time intervals to produce a set of integrated pixel signals at the end of each said time interval, whereby pixel signals proportional to the amount of the X-rays received by their respective areas of the radiation detector are provided during each said variable time interval;

(f) dumping the set of integrated pixel data signals from the detector to a preamplifier for amplification at the end of each said variable time interval;

(g) converting each integrated pixel data signal into a corresponding digital signal; and (h) processing the digital signals to produce the panoramic digital X-ray image of the object.

12. The method of claim 11 wherein said rotation center is moving in relation to said object.

* * * * *

UNITED STATES PATENT AND TRADEMARK OFFICE
CERTIFICATE OF CORRECTION

PATENT NO.   :   5,018,177

DATED        :   July 8, 1991

INVENTOR(S)  :   McDavid, et al.

It is certified that error appears in the above-identified patent and that said Letters Patent is hereby corrected as shown below:

Claim 11, line 46, column 10, change "ρ" to --τ--.

Signed and Sealed this

Twenty-ninth Day of December, 1992

*Attest:*

DOUGLAS B. COMER

*Attesting Officer*   Acting Commissioner of Patents and Trademarks